USO10435412B2

United States Patent
Jagerovic et al.

(10) Patent No.: US 10,435,412 B2
(45) Date of Patent: Oct. 8, 2019

(54) SELECTIVE MODULATORS OF THE ACTIVITY OF THE GPR55 RECEPTOR: CHROMENOPYRAZOLE DERIVATIVES

(71) Applicants: Consejo Superior de Investigaciones Cientificas (CSIC), Madrid (ES); The Governing Council of the University of Toronto, Toronto, Ontario (CA)

(72) Inventors: Nadine Jagerovic, Madrid (ES); Paula Morales Lazaro, Madrid (ES); Ruth Ross, Toronto (CA); Lauren Whyte, Toronto (CA)

(73) Assignees: THE GOVERNING COUNCIL OF THE UNIVERSITY OF TORONTO, Toronto, Ontario (CA); CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 0 days.

(21) Appl. No.: 15/571,671

(22) PCT Filed: Apr. 27, 2016

(86) PCT No.: PCT/ES2016/070314
§ 371 (c)(1),
(2) Date: Nov. 3, 2017

(87) PCT Pub. No.: WO2016/177922
PCT Pub. Date: Nov. 10, 2016

(65) Prior Publication Data
US 2018/0201620 A1    Jul. 19, 2018

(30) Foreign Application Priority Data

May 5, 2015 (ES) .................................. 201530608

(51) Int. Cl.
| | | |
|---|---|---|
| *C07D 491/052* | (2006.01) | |
| *A61K 31/4162* | (2006.01) | |
| *A61P 25/04* | (2006.01) | |
| *A61P 3/10* | (2006.01) | |
| *A61P 25/16* | (2006.01) | |
| *A61P 19/10* | (2006.01) | |
| *A61P 35/00* | (2006.01) | |

(52) U.S. Cl.
CPC ...... *C07D 491/052* (2013.01); *A61K 31/4162* (2013.01); *A61P 3/10* (2018.01); *A61P 19/10* (2018.01); *A61P 25/04* (2018.01); *A61P 25/16* (2018.01); *A61P 35/00* (2018.01)

(58) Field of Classification Search
CPC ...... A61K 31/4162; A61P 19/10; A61P 25/04; A61P 25/16; A61P 35/00; A61P 3/10; C07D 491/052
See application file for complete search history.

(56) References Cited

FOREIGN PATENT DOCUMENTS

| | | |
|---|---|---|
| ES | 2548789 A1 | 10/2015 |
| WO | 01/86305 A2 | 11/2001 |
| WO | 2004074844 A1 | 9/2004 |
| WO | 2010109050 A1 | 9/2010 |
| WO | 2014013117 A1 | 1/2014 |

OTHER PUBLICATIONS

Johnson et al., (British J. of Cancer 2001, p. 1424-1431) (Year: 2001).*
Gura et al. (Science Nov. 7, 1997, 278) (Year: 1997).*
Neidle, Stephen, ed., Cancer Drug Design and Discovery:(Elsevier/Academic Press, 2008) (Year: 2008).*
Cecil Textbook of Medicine, 20th Edition, vol. 1, 1996 (Year: 1996).*
Cumella; "Chromenopyrazoles: Non-Psychoactive and Selective CB1 Cannabinoid Agonists With Peripheral Antinociceptive Properties"; ChemMedChem; Mar. 5, 2012; p. 452-463; vol. 7 Issue 3; NIH Public Access.
Press; "Heterocyclic-fused Benzopyrans as Cannabinoid Analogues"; J. Heterocyclic Chem; Mar.-Apr. 1985; p. 561-564;Medical Research Division of American Cyanamid Company.

* cited by examiner

*Primary Examiner* — Umamaheswari Ramachandran
(74) *Attorney, Agent, or Firm* — Tristan A. Fuierer; Olive Law Group PLLC (57) ABSTRACT

The present invention relates to a family of chromenopyrazole derivatives of formula (I):

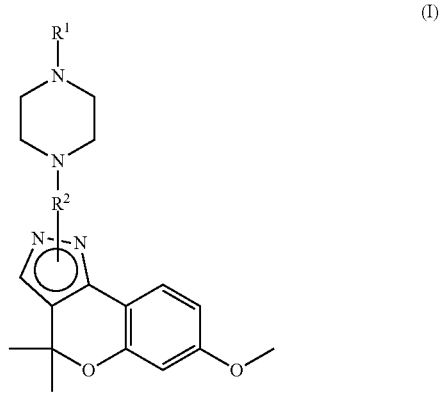

which have the ability to modulate the receptor of the cannabinoid family GPR55, whereby the invention also relates to the use of these compounds for the manufacture of a medicament for the treatment of diseases in which the GPR55 receptor has a physiological role such as diabetes, Parkinson's disease, multiple sclerosis, neuropathic pain, osteoporosis and cancers such as cholangiocarcinoma, breast cancer, ovarian and prostate cancer, glioblastoma, and cutaneous carcinoma.

19 Claims, 3 Drawing Sheets

SELECTIVE MODULATORS OF THE ACTIVITY OF THE GPR55 RECEPTOR: CHROMENOPYRAZOLE DERIVATIVES

FIELD OF INVENTION

The present invention is in the field of pharmacology. Specifically, the present invention relates to piperazines derived from 7-methoxy-4,4-dimethyl-1,4-dihydrochromeno [4,3-c] pyrazole and 7-methoxy-4,4-dimethyl-2,4-dihydrochromene [4,3-c] pyrazole, its use for the manufacture of a medicament, the use of this medicament for the treatment and/or prevention of a disorder associated with the GPR55 receptor and the use of these compounds for pharmacological assays related to GPR55.

BACKGROUND OF THE INVENTION

The GPR55 receptor was cloned and first identified in 1999. It is a G protein-coupled transmembrane receptor. Although it shares only 14% homology with the CB1 and CB2 cannabinoid receptors, it was proposed as a new member of the endocannabinoid system. Indeed, cannabinoid receptor ligands were found to be able to activate the GPR55 receptor (GlaxoSmithKline WO0186305; AstraZeneca WO2004074844). Currently, there is controversy surrounding the pharmacology of GPR55. Today, GPR55 is still considered an orphaned receptor. However, endogenous lysophosphatidylinositol (LPI) derivatives have been reported to stimulate the GPR55 receptor in ERK1/2 phosphorylation assays in HEK293 cells overexpressing hGPR55. To date, there are very few GPR55 receptor specific agonists and/or antagonists. Some benzoylpiperazine derivatives were identified as GPR55 agonists with no action on the CB1 and CB2 cannabinoid receptors. A high screening pharmacological evaluation using β-arrestin assays in hGPR55-U2OS cells identified several families of GPR55 agonists and selective GPR55 antagonists that led to molecular modeling studies.

The GPR55 receptor has been shown to be involved in the processes of inflammatory pain, neuropathic pain, metabolic disorder, bone development, and tumor cell proliferation. Therefore, GPR55 is considered a biological target for the treatment of GPR55-related diseases such as diabetes, Parkinson's disease, multiple sclerosis, neuropathic pain, osteoporosis, cholangiocarcinoma, breast cancer, ovarian and prostate cancer, glioblastoma, and cutaneous carcinoma.

The compounds claimed in the present invention are chromenopyrazole-based structures. WO2010109050 describes chromenopyrazoles as cannabinoids with analgesic activity. More recently, in WO2014013117 and P201430372 chromenopyrazoles are described as antitumor drugs related to cannabinoid activity.

DESCRIPTION OF THE INVENTION

The present invention disclosed novel compounds useful as pharmacological tools for the validation of the GPR55 receptor and as therapeutic agents related to GPR55. The novel compounds of the present invention act on GPR55 receptors. Thus, they are useful for treating GPR55 receptor-related diseases and disorders, such as diabetes, Parkinson's disease, multiple sclerosis, neuropathic pain, osteoporosis, cholangiocarcinoma, breast cancer, ovarian cancer and prostate cancer, glioblastoma and cutaneous carcinoma.

The inventors of the present invention have found that the compounds of formula (I) act on the orphan receptor GPR55 selectively and thus are useful for modulating processes in which GPR55 is involved.

In one aspect, the present invention relates to a compound of general formula (I)

Formula (I)

or a tautomer, a pharmaceutically acceptable salt or solvate thereof; wherein:

$R^1$ is selected from optionally substituted aryl or a group —C(O)$R^3$; $R^3$ is selected from aryl, heterocycle, $C_1$-$C_6$ alkyl, $C_3$-$C_6$ cycloalkyl or a —(CH$_2$)$_n$—O-aryl group, wherein n is a value selected from 1, 2, 3 or 4.

$R^2$ is selected from $C_1$-$C_6$ alkylene group or a —$R^4$—C(O)—NH—$R^5$-group, being $R^4$ and $R^5$ the same or different $C_1$-$C_6$ alkylene group.

Another aspect of the invention relates to a compound of general formula (II)

Formula (II)

or a tautomer, a pharmaceutically acceptable salt, or solvate thereof; where $R^1$ and $R^2$ are as defined above.

Another aspect of the present invention relates to a compound of general formula (III)

Formula (III)

or a tautomer, a pharmaceutically acceptable salt, or solvate thereof; wherein $R^1$ and $R^2$ are as defined above.

In a preferred embodiment, $R^1$ is a —C(O)$R^3$ group wherein $R^3$ is any of the above-mentioned possibilities, although preferably $R^3$ is aryl and more preferably phenyl.

In another preferred embodiment, $R^3$ is heterocyclic and more preferably $R^3$ is selected from furan, thiophene or tetrahydrofuran.

In another preferred embodiment, $R^3$ is cyclohexyl.

In another preferred embodiment, $R^3$ is $C_1$-$C_4$ alkyl.

In another preferred embodiment, $R^2$ is $C_1$-$C_4$ alkylene, and more preferably ethylene.

According to a preferred embodiment, the compound of formula (I) is selected from the following list:
1-(2-(4-(2-furoyl)piperazinyl)ethyl)-1,4-dihydro-7-methoxy-4,4-dimethylchromeno[4,3-c]pyrazole
2-(2-(4-(2-furoyl)piperazinyl)ethyl)-2,4-dihydro-7-methoxy-4,4-dimethylchromeno[4,3-c]pyrazole
1-(2-(4-benzoyl-piperazinyl)ethyl)-1,4-dihydro-7-methoxy-4,4-dimethylchromeno[4,3-c]pyrazole
2-(2-(4-benzoyl-piperazinyl)ethyl)-2,4-dihydro-7-methoxy-4,4-dimethylchromeno[4,3-c]pyrazole
1-(2-(4-(2-thienoyl)piperazinyl)ethyl)-1,4-dihydro-7-methoxy-4,4-dimethylchromeno[4,3-c]pyrazole
2-(2-(4-(2-thienoyl)piperazinyl)ethyl)-2,4-dihydro-7-methoxy-4,4-dimethylchromeno[4,3-c]pyrazole
2-(2-(4-phenoxyacetylpiperazinyl)ethyl)-2,4-dihydro-7-methoxy-4,4-dimethylchromeno[4,3-c]pyrazole
2-(2-(4-(2-tetrahydrofuroyl)piperazinyl)ethyl)-2,4-dihydro-7-methoxy-4,4-dimethylchromeno[4,3-c]pyrazole
2-(2-(4-cyclohexylcarbonyl-piperazinyl)ethyl)-2,4-dihydro-7-methoxy-4,4-dimethylchromeno[4,3-c]pyrazole
2-(2-(4-pivaloyl-piperazinyl)ethyl)-2,4-dihydro-7-methoxy-4,4-dimethylchromeno[4,3-c]pyrazole In another preferred embodiment, $R^1$ is an optionally substituted phenyl. In a more preferred embodiment, $R^1$ is a phenyl substituted by a $C_1$-$C_4$ alkyl or a $C_1$-$C_4$ alkyloxy and more preferably by a methyl or a methoxy.

In another preferred embodiment $R^2$ is a group —$R^4$—C(O)—NH—$R^5$—, being $R^4$ and $R^5$ the same or different $C_1$-$C_4$ alkylene. In a more preferred embodiment, $R^4$ and $R^5$ are methylene.

According to a preferred embodiment, the compound of formula (II) is selected from the following list:
1-(2-(4-phenylpiperazinyl)acetamidomethyl)-1,4-dihydro-7-methoxy-4,4-dimethylchromeno[4,3-c]pyrazole
2-(2-(4-phenylpiperazinyl)acetamidomethyl)-2,4-dihydro-7-methoxy-4,4-dimethylchromeno[4,3-c]pyrazole
1-(2-(4-(2-methoxyphenyl)piperazinyl)acetamidomethyl)-1,4-dihydro-7-methoxy-4,4-dimethylchromeno[4,3-c]pyrazole
2-(2-(4-(2-methoxyphenyl)piperazinyl)acetamidomethyl)-2,4-dihydro-7-methoxy-4,4-dimethylchromeno[4,3-c]pyrazole
1-(2-(4-(2,3-dimethylphenyl)piperazinyl)acetamidomethyl)-1,4-dihydro-7-methoxy-4,4-dimethylchromeno[4,3-c]pyrazole
2-(2-(4-(2,3-dimethylphenyl)piperazinyl)acetamidomethyl)-2,4-dihydro-7-methoxy-4,4-dimethylchromeno[4,3-c]pyrazole
1-(2-(4-(4-methoxyphenyl)piperazinyl)acetamidomethyl)-1,4-dihydro-7-methoxy-4,4-dimethylchromeno[4,3-c]pyrazole.

The term "alkyl" refers, in the present invention, to saturated or unsaturated aliphatic, linear, cyclized or branched chains having 1 to 6 carbon atoms. For example, but not limited to, the alkyl group may be methyl, ethyl, cyclohexane, etc. The alkyl groups may be optionally substituted by one or more substituents such as halogen, hydroxyl or carboxylic acid.

The term "aryl" refers, in the present invention, to single or multiple aromatic rings having from 5 to 18 bonds in which a proton has been removed from the ring. Aryl groups are, for example, but not limited to, phenyl, naphthyl, diphenyl, indenyl, phenanthryl or anthracyl. Preferably the aryl group has 5 to 7 carbon atoms and more preferably the aryl group is a phenyl. The aryl radicals may be optionally substituted by one or more substituents such as ($C_1$-$C_6$) alkyl, alkoxy, halogen, hydroxyl or carboxylic acid and more preferably the aryl group is substituted by one or two methoxy groups.

The term "cycloalkyl" refers, in the present invention, to cyclic hydrocarbon chain radicals, preferably with 3 to 6 carbon atoms, and more preferably 6, which is saturated or partially saturated, and which consists only of carbon and hydrogen atoms, such as cyclopropyl, cyclopentyl or cyclohexyl and which may be optionally substituted by one or more groups such as alkyl, halogens, hydroxyl, amines, amides, cyano etc.

The term "heterocycle" refers, in the present invention, to a cyclic structure containing from 1 to 4 heteroatoms selected from nitrogen, oxygen and sulfur. The structure may be aromatic or hydrogenated. Preferably, the heterocycle may be selected from thienyl, furyl, tetrahydrofuryl, pyridyl, imidazolyl, pyrazolyl, morpholino but not limited to. Heterocyclic radicals may be optionally substituted by one or more substituents such as ($C_1$-$C_6$) alkyl, alkoxy, halogen, hydroxyl or carboxylic acid.

Unless otherwise noted, the compounds of the invention also relate to including compounds which differ only in the presence of one or more isotopically enriched atoms. For example, compounds having the present structures, with the exception of the substitution of a hydrogen by a deuterium or by tritium, or the substitution of a carbon by a $^{13}$C or $^{14}$C enriched carbon or a $^{15}$N enriched nitrogen, are within the scope of this invention.

The term "tautomer" or "tautomeric form", as used herein, refers to structural isomers of different energies that are interconvertible via a low energy barrier. For example, proton tautomers (also known as prototropic tautomers) including interconversions by the migration of a proton, such as keto-enolic or imine-enamine isomerizations. Valence tautomers include interconversions by rearrangement of some binding electrons.

The term "pharmaceutically acceptable salts or solvates" refers to any pharmaceutically acceptable salt, ester, solvate, or any other compound which, when administered to a recipient is capable of providing (directly or indirectly) a compound as described herein document. However, it will be appreciated that pharmaceutically unacceptable salts are also within the scope of the invention since they may be useful in the preparation of pharmaceutically acceptable salts. The preparation of salts and derivatives may be carried out by methods known in the art.

For example, pharmaceutically acceptable salts of compounds provided herein are synthesized by conventional chemical methods from an original compound containing a basic moiety or acid. Generally, such salts are prepared, for example, by reacting the acid or free base forms of the compounds with a stoichiometric amount of the appropriate base or acid in water or in an organic solvent or a mixture of the two. Generally, non-aqueous media such as ether, ethyl acetate, ethanol, isopropanol or acetonitrile are preferred. Examples of acid addition salts include mineral acid addition salts such as, for example, hydrochloride, hydrobromide, hydroiodide, sulfate, nitrate, phosphate and organic acid addition salts such as, for example, acetate, maleate, fumarate, citrate, oxalate, succinate, tartrate, malate, mandelate, methanesulfonate and p-toluenesulfonate. Examples of base addition salts include inorganic salts such as, for example, sodium, potassium, calcium, ammonium, magnesium, aluminum and lithium salts, and salts of organic bases such as, for example, ethylenediamine, ethanolamine, N,N-dimethylethanolamine, triethanolamine, glucamine and salts of basic amino acids.

Particularly preferred derivatives are those which increase the bioavailability of the compounds of this invention when such compounds are administered to a patient (for example, by causing a compound administered orally to be more readily absorbed into the blood), or potentiating the release of the original compound in a biological compartment (e.g. brain or lymphatic system) relative to the original species.

The compounds of formula (I), (II) or (III) may be in crystalline form as free compounds or as solvates and both forms are intended to be within the scope of the present invention. Methods of solvation are generally known within the art. Suitable solvates are pharmaceutically acceptable solvates. In a particular embodiment, the solvate is a hydrate.

The compounds of formula (I), of formula (II) and of formula (III) or their salts or solvates are preferably in a pharmaceutically acceptable form or substantially pure. By pharmaceutically acceptable form is meant, inter alia, that they have a pharmaceutically acceptable level of purity excluding normal pharmaceutical additives such as diluents and carriers, and not including material considered toxic at normal dosage levels. The purity levels for the active ingredient are preferably above 50%, more preferably above 70%, more preferably above 90%. In a preferred embodiment, they are greater than 95% of the compound of formula (I), or salts thereof.

The compounds of formula (I) of formula (II) and formula (III) defined above can be obtained by a combination of synthetic reactions known in the art such as those mentioned in the article Press JB, J. Heterocyclic Chem., 1985, 22, 561-564.

In another aspect, the present invention relates to the use of a compound of formula (I), of formula (II) or of formula (III) for the manufacture of a medicament.

In another aspect, the present invention relates to the use of a compound of formula (I), of formula (II) or of formula (III) for the manufacture of a medicament for the treatment and/or prevention of a disorder associated with GPR55 receptors.

According to a preferred embodiment, the disorder associated with GPR55 receptors is selected from diabetes, Parkinson's disease, multiple sclerosis, neuropathic pain, osteoporosis, cholangiocarcinoma, breast cancer, ovarian and prostate cancer, glioblastoma and cutaneous carcinoma.

In another aspect, the present invention relates to a compound of formula (I) or formula (II) or formula (III) for use in the treatment of and/or prevention of a disorder associated with cannabinoid receptors.

The term "disorder" as used in the present invention refers to the presence of a behavior or group of symptoms identifiable in clinical practice, which in most cases are accompanied by discomfort or interfere with the habitual activity of the individual.

The compounds of formula (I), of formula (II) or of formula (III), their pharmaceutically acceptable salts or solvates thereof, can therefore be used in the prevention and/or treatment of a disorder requiring modulation of the GPR55 receptors. Pharmaceutical compositions containing a therapeutically effective amount of a compound of formula (I) or formula (II), their pharmaceutically acceptable salts or solvates thereof, together with the pharmaceutically acceptable excipients constitute a further aspect of the present invention.

The amount of the compound of formula (I), formula (II) or formula (III), the pharmaceutically acceptable salts or solvates thereof, therapeutically effective to be administered as well as its dosage for treating a disease state with said compounds will depend on numerous factors, including age, patient status, severity of disease, route and frequency of administration, modulator compound to be used, etc.

In another aspect, the present invention also relates to pharmaceutical compositions comprising at least one compound of the invention, or a tautomer, a pharmaceutically acceptable salt, a solvate or a prodrug thereof, together with a pharmaceutically acceptable carrier or carrier, an excipient or a vehicle, for administration to a patient.

In a preferred embodiment, the pharmaceutical composition further comprises another active ingredient.

Some examples of the pharmaceutical compositions are solids (tablets, pills, capsules, granular solid, etc.) or liquids (solutions, suspensions or emulsions) prepared for oral, nasal, topical or parenteral administration.

In a preferred embodiment of the present invention, the pharmaceutical compositions are suitable for oral administration, in solid or liquid form. Possible forms for oral administration are tablets, capsules, syrups or solutions and may contain conventional excipients known in the pharmaceutical field as binders (e.g. syrup, acacia, gelatin, sorbitol, tragacanth or polyvinyl pyrrolidone), fillers (e.g. lactose, sugar, corn starch, calcium phosphate, sorbitol or glycine), disintegrating agents (e.g. starch, polyvinyl pyrrolidone or microcrystalline cellulose) or a pharmaceutically acceptable surfactant such as sodium lauryl sulfate.

Compositions for oral administration may be prepared by the conventional methods of Galenic Pharmacy as a mixture and dispersion. The tablets may be coated following methods known in the pharmaceutical industry.

The pharmaceutical compositions may be adapted for parenteral administration, as sterile solutions, suspensions, or lyophilizates of the products of the invention, using the appropriate dosage. Suitable excipients may be employed, such as pH buffering agents or surfactants.

Administration of the compounds or compositions of the present invention may be accomplished by any suitable method, such as intravenous infusion and oral, intraperitoneal or intravenous routes. Oral administration is preferred because of the convenience of patients and the chronic nature of the diseases to be treated.

The administered amount of a compound of the present invention will depend upon the relative efficacy of the compound selected, the severity of the disease to be treated and the patient's weight. However, the compounds of this invention will be administered one or more times a day, for example 1, 2, 3 or 4 times daily, with a total dose between 0.1 and 1000 mg/kg/day. It is important to note that dose variations may be necessary, depending on the patient's age and condition, as well as changes in the route of administration.

The compounds and compositions of this invention may be used alone or in combination with other drugs to provide a combination therapy. The other drugs may form part of the same composition, or be provided as a separate composition, for administration at the same time or at a different time.

A combination therapy may be of particular interest because of the type of pathologies to be treated with these compounds as defined herein, these pathologies are especially complex, since patients generally exhibit a combination of symptoms as well as a variety of damages or alterations. Therefore, it may be of interest to combine several drugs, each directed to specifically prevent, alleviate or cure a particular symptom, damage or alteration, or also to several of them, resulting in a combined therapy directed at the disease or condition of a form global, taking into account many, most, or all aspects involved in it.

Drugs to be combined with the compounds of the present invention may be approved drugs for the treatment of any of the diseases, or be newly developed.

In another aspect, the present invention relates to the use of a compound of formula (I), of formula (II) or of formula (III) for the manufacture of a reagent in biological assays related to GPR55 receptor.

In the present invention, the term "reagent" refers to a test substance which is added to a system to give rise to a reaction or to check whether a reaction occurs.

In the present invention, the term "biological assay" refers to a method for measuring a substance, either quantitatively or qualitatively, in a living or in vitro organism. Qualitative tests are used to determine the physical effects of a substance in that organism. Quantitative tests are used for the estimation of the concentration or potency of a substance by measuring the biological response produced by that substance.

Throughout the description and claims the word "comprises" and its variants are not intended to exclude other technical features, additives, components or steps. Other objects, advantages and features of the invention will be apparent to those skilled in the art in part from the description and in part from the practice of the invention. The following examples and figures are given by way of illustration and are not intended to be limiting of the present invention.

EXAMPLES

Figure 1:
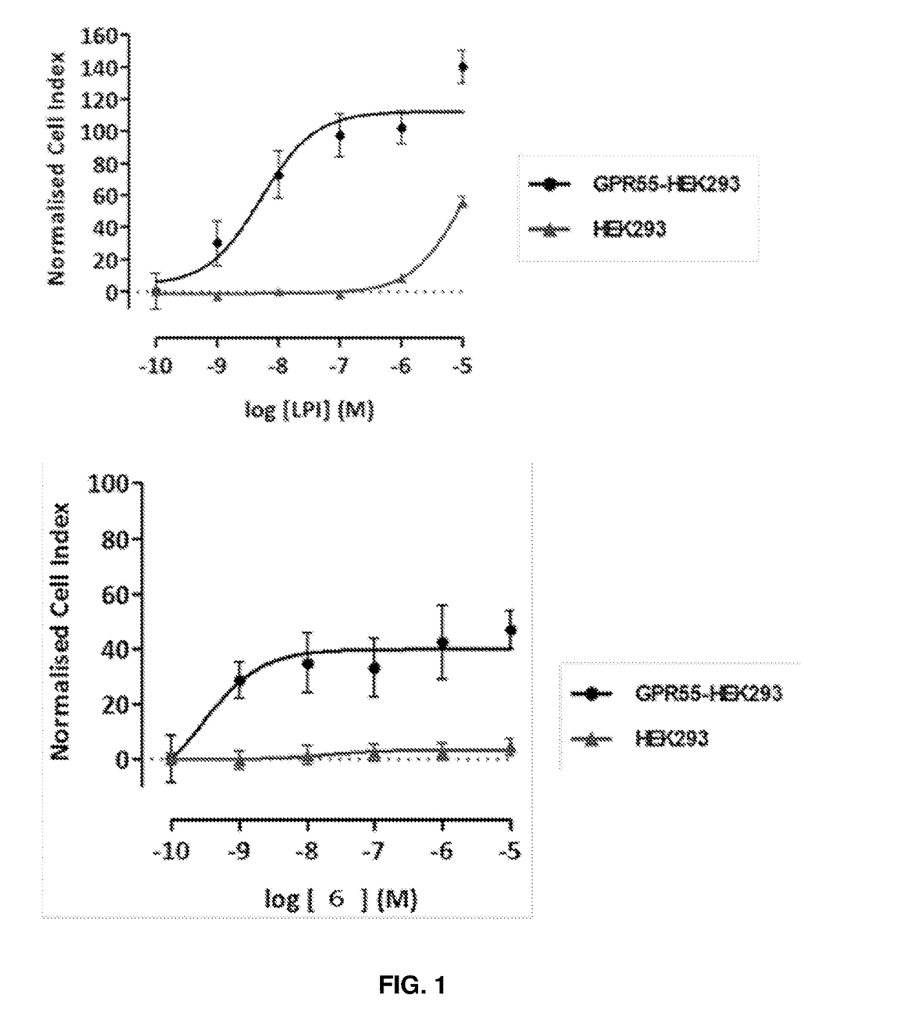
FIG. 1. LPI concentration-response curves and Examples 2, 6 and 8 in hGPR55-HEK293 and HEK293 cells. Values represent the mean±SEM from 4 independent experiments performed in duplicate. The values correspond to a percentage of the maximum stimulation produced by LPI.
Figure 2:
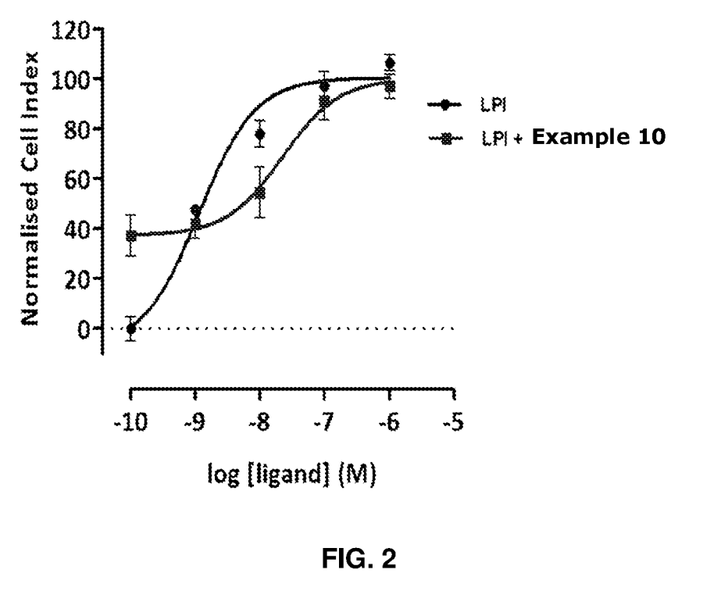
FIG. 2. Concentration-response curve in the presence or absence of LPI from Example 10 in hGPR55-HEK293 cells. Values represent the mean±SEM from 4 independent experiments performed in duplicate. The values correspond to a percentage of the maximum stimulation produced by LPI.

The invention will now be illustrated by assays carried out by the inventors, which shows the effectiveness of the product of the invention.

General Methods

Purification of the reaction products was performed by column chromatography using silica gel 60 Merck 230-400 mesh. The separation by semi-preparative high-performance liquid chromatography was performed on a Waters chromatograph integrated by a 2767 Sample Manager injector/manifold module, a System Fluidic Organizer separation module, a Photodiode Array 2998 (UV-visible) detector and a mass spectrophotometer 3100 Mass Detector. A SunFire™ C18 reverse phase column (19 mm×150 mm) is used for the separation. The mobile phases used are: A (MeCN+0.1% formic acid) and B (H2O+0.1% formic acid). The gradient was performed using a flow of 24 mL/min in 70 minutes monitoring at λ=254 nm. Exact mass spectra were recorded on an Agilent Technologies 6520 Accurate-Mass QTOF LC/MS spectrometer with a positive electrospray source. NMR analyzes were performed in the deuterated solvent indicated in each case. $^{13}$C-NMR, heteronuclear correlation HMBC and HSQC were recorded on a Mercury 400 (400 and 101 MHz) or Varian 500 (500 and 126 MHz) spectrometers at 25° C. The melting points were measured on an MP70 Mettler Toledo apparatus.

The starting product for the preparation of the compounds of formula (I) of the present invention is 7-methoxy-4,4-dimethyl-1,4-dihydrochromeno [4,3-c]pyrazole. To synthesize the 7-methoxy-4,4-dimethyl-1,4-dihydrochromeno[4,3-c]pyrazole, the 2-hydroxy-4-methoxyacetophenone was cyclized with acetone. A-Formylation of 7-methoxy-2,2-dimethyl-2,3-dihydrochromen-4-one with microwave irradiation led to 3-hydroxymethylenecromen-4-one. Finally, condensation with anhydrous hydrazine gave the 7-methoxy-4,4-dimethyl-1,4-dihydrochromeno[4,3-cpyrazole.

The synthetic route for preparing 7-methoxy-4,4-dimethyl-1,4-dihydrochromeno[4,3-c]pyrazole is summarized in the following scheme (I):

Scheme (I)

-continued

Preparation of 7-methoxy-4,4-dimethyl-1,4-dihydro-chromeno[4,3-c]pyrazole

A solution of 3-(hydroxymethylene)-7-methoxy-2,2-dimethylchroman-4-one (1.46 g, 6.27 mmol) and anhydrous hydrazine (0.58 mL, 83 mmol) in EtOH was stirred at 60° C. for 2 hours. After evaporation of the solvent under vacuum, the crude was purified by medium pressure chromatography on silica gel (hexane/AcOEt, 1:1). 7-Methoxy-4,4-dimethyl-1,4-dihydrochromeno[4,3-c]pyrazole (0.99 g, 69%) was obtained as a white solid. mp: 158-160° C. MS (ES+, m/z) 231 [M+H]+.

A. Preparation of 1-(2-(4-(2-ketone)piperazinyl)ethyl)-1,4-dihydro-7-methoxy-4,4-dimethyl-chromene[4,3-c]pyrazoles of Formula (III) and 2-(2-(4-(2-ketone)piperazinyl)ethyl)-1,4-dihydro-7-methoxy-4,4-dimethylchromeno[4,3-c]pyrazole of Formula (I) wherein $R^1$ is a —C(O)$R^3$ Group For the synthesis of 1-(2-(4-(2-ketone)piperazinyl)ethyl)-1,4-dihydro-7-methoxy-4,4-dimethylchromeno[4,3-c]pyrazoles of formula (III) and 1-(2-(4-(2-ketone) piperazinyl) ethyl)-1,4-dihydro-7-methoxy-4,4-dimethylchromeno[4,3-c]pyrazoles of formula (IV) of the present invention, 7-methoxy-4,4-dimethyl-1,4-dihydrochromeno[4,3-c]pyrazole was alkylated with 1,2-dibromoethane. The 2 regioisomers obtained, 1-(2-bromoethyl)-7-methoxy-4,4-dim ethyl-1,4-dihydrochromeno[4,3-c]pyrazole and 2-(2-bromoethyl)-7-methoxy-4,4-dimethyl-1,4-dihydrochromeno[4,3-c] pyrazole were isolated by chromatography. Finally, reaction with the acylpiperazines led to the exemplary compounds of formula (III) and to the exemplary compounds of formula (IV).

This procedure is summarized in the following scheme (II):

Scheme (II)

Preparation of 1-(2-bromoethyl)-7-methoxy-4,4-dimethyl-1,4-dihydrochromeno[4,3-c pyrazole and 2-(2-bromoethyl)-7-methoxy-4-, 4-dimethyl-1,4-dihydrochromeno[4,3-c] pyrazole A suspension of NaH (28 mg, 1.19 mmol) in dry THF was added to a solution of 7-methoxy-4,4-dimethyl-1,4-dihydrochromeno[4,3-c]pyrazole (0.23 g, 0.99 mmol) in THF. The mixture was heated under reflux for 4 h. The solvent was removed under vacuum. The crude oil dissolved in AcOEt was washed with water, dried with $MgSO_4$ and the solvent was evaporated under vacuum. Chromatography on silica gel (hexane/AcOEt, 1:1) led to the separation of the 2 isomers, 1-(2-bromoethyl)-7-methoxy-4,4-dimethyl-1,4-dihydrochromeno[4,3-c]pyrazole and 2-(2-bromoethyl)-7-methoxy-4,4-dimethyl-1,4-dihydrochromeno[4,3-c]pyrazole.

1-(2-Bromoethyl)-7-methoxy-4,4-dimethyl-1,4-dihydrochromeno[4,3-c]pyrazole (75 mg, 20%); $^1$H NMR (400 MHz, $CDCl_3$) δ: 7.34 (d, J=7.9 Hz, 1H), 7.22 (s, 1H), 6.50 (dd, J=7.9, 2.4 Hz, 1H), 6.43 (d, J=2.4 (T, J=6.6 Hz), 3.92 (s, 3H), 1.45 (s, 6H) ppm; $^{13}$C-NMR (101 MHz, $CDCl_3$) δ: 161.7, 155.3, 144.7, 133.4, 123.9, 121.9, 108.5, 103.4, 101.8, 76.7, 59.3, 55.8, 29.6, 28.5 ppm; MS (ES$^+$, m/z) 337 [M+H]$^+$; HRMS $C_{15}H_{17}BrN_2O_2$: content. 336.0473, exp. 336.0478.

2-(2-Bromoethyl)-7-methoxy-4,4-dimethyl-1,4-dihydrochromeno[4,3-c]pyrazole (0.19 g, 51%); $^1$H-NMR (400 MHz, $CDCl_3$) δ: 7.68 (d, J=8.4 Hz, 1H), 7.32 (s, 1H), 6.63 (dd, J=8.4, 2.5 Hz, 1H), 6.58 (d, J=2.5 Hz, 1H), 4.54 (t, J=6.5 Hz, 2H), 3.86 (s, 3H), 3.80 (t, J=6.5 Hz, 2H), 1.66 (s, 6H) ppm; $^{13}$C-NMR (101 MHz, $CDCl_3$) δ: 161.1, 154.7, 143.8, 124.6, 123.2, 120.9, 110.9, 108.1, 103.2, 76.6, 55.5, 53.8, 30.7, 29.4 ppm; MS (ES$^+$, m/z) 337 [M+H]$^+$; HRMS $C_{15}H_{17}BrN_2O_2$: content. 336.0473, exp. 336.0470.

Example 1—Preparation of 1-(2-(4-(2-furoyl)piperazinyl)ethyl)-1,4-dihydro-7-methoxy-4,4-dimethylchromeno[4,3-c]pyrazole 1-(2-Furoyl)piperazine (12 mg, 0.06 mmol) and $K_2CO_3$ (27 mg, 0.19 mmol) dissolved in THF was stirred at room temperature for 10 min. A solution of 1-(2-bromoethyl)-7-methoxy-4,4-dimethyl-1,4-dihydrochromeno[4,3-c]pyrazole (22 mg, 0.06 mmol) in THF was added to the mixture and heated at reflux overnight. The solvent was evaporated under vacuum. The crude oil dissolved in EtOAc was washed with water, dried over $MgSO_4$, and after filtration the solvent was evaporated. 1-(2-(4-(2-Furoyl)piperazinyl)ethyl)-1,4-dihydro-7-methoxy-4,4-dimethylchromene [4,3-c] pyrazole was isolated by medium pressure chromatography (7 mg, 25%); $^1$H-NMR ($CDCl_3$) δ: 7.57 (d, J=8.5 Hz), 7.33-7.28 (m, 1H), 7.11 (s, 1H), 6.96-6.92 (m, 1H), 6.60 (dd, J=8.5) 1H), 6.39-6.36 (m, 1H), 4.22 (t, J=6.6 Hz, 2H), 3.78 (s, 3H), 3.39-3.21 (m, 4H), 2.83 (t, J=6.6 Hz, 2H), 2.72-2.64 (m, 4H), 1.52 (s, 6H) ppm; $^{13}$C-NMR (101 MHz, $CDCl_3$) δ: 162.0, 155.6, 153.1, 145.3, 142.6, 141.8, 124.1, 123.2, 121.3, 117.0, 112.2, 109.2, 108.4, 103.2, 76.1, 57.5, 55.1, 54.1, 50.7, 49.5, 28.9 ppm; MS (ES$^+$, m/z) 437 [M+H]$^+$; HRMS $C_{24}H_{28}N_4O_4$: content. 436.2110, exp. 436.2107.

Example 2—Preparation of 2-(2-(4-(2-furoyl)piperazinyl)ethyl)-2,4-dihydro-7-methoxy-4,4-dimethylchromeno[4,3-c]pyrazole The desired compound was prepared according to the procedure described for Example 1 using 2-(2-bromoethyl)-7-methoxy-4,4-dimethyl-1,4-dihydrochromeno[4,3-c]pyrazole (20 mg, 0.06 mmol) and 1-(2-furoyl)piperazine (11 mg, 0.06 mmol). Yellow oil (6 mg, 24%); $^1$H NMR (400 MHz, $CDCl_3$) δ: 7.61 (d, J=8.4 Hz, 1H), 7.48-7.45 (m, 1H), 7.18 (s, 1H), 7.00-6.94 (m, 1H), 6.54 (dd, J=8.4, 2.5 Hz, 1H), 6.50 (d, J=2.5 Hz, 1H), 6.46-6.44 (m, 1H), 4.23 (t, J=6.5 Hz, 2H), 3.76-3.62 (s, 7H), 2.86 (t, J=6.5 Hz, 2H), 2.70-2.66 (m, 4H), 1.58 (s, 6H) ppm; $^{13}$C-NMR (101 MHz, $CDCl_3$) δ: 160.9, 159.3, 154.5, 148.0, 143.9, 142.9, 124.2, 123.1, 121.0, 116.7, 111.5, 111.2, 108.0, 103.2, 76.7, 58.0, 55.5, 53.6, 51.3, 50.4, 29.5 ppm; MS (ES$^+$, m/z) 437 [M+H]$^+$; HRMS $C_{24}H_{28}N_4O_4$: content. 436.2110, exp. 436.2121.

Example 3—Preparation of 1-(2-(4-benzoyl-piperazinyl)ethyl)-1,4-dihydro-7-methoxy-4,4-dimethylchromeno[4,3-c]pyrazole The desired compound was prepared according to the procedure described for Example 1 using 1-(2-bromoethyl)-7-methoxy-4,4-dimethyl-1,4-dihydrochromeno[4,3-c]pyrazole (20 mg, 0.06 mmol) and benzoylpiperazine (11 mg, 0.06 mmol). Yellow amorphous solid (8 mg, 30%); $^1$H-NMR ($CDCl_3$) δ: 7.55 (d, J=8.4 Hz, 1H), 7.38-7.29 (m, 5H), 7.13 (s, 1H), 6.49 (dd, J=8.4, 2.5 Hz, J=6.7 Hz, 2H), 3.73 (s, 3H), 3.41-3.26 (m, 4H), 2.81 (t, J=6.7 Hz, 2H)), 2.59-2.37 (m, 4H), 1.52 ppm (s, 6H); $^{13}$C-NMR (101 MHz, $CDCl_3$) δ: 170.3, 165.1, 160.7, 154.3, 130.2, 129.7, 128.5, 127.1, 124.4, 123.9, 122.8, 107.9, 107.6, 103.0, 76.4, 57.8, 55.4, 55.3, 53.6, 50.1, 29.2 ppm; MS (ES$^+$, m/z) 447 [M+H]$^+$; HRMS $C_{26}H_{30}N_4O_3$: content. 446.2317, exp. 446.2324.

Example 4—Preparation of 2-(2-(4-benzoyl-piperazinyl)ethyl)-2,4-dihydro-7-methoxy-4,4-dimethylchromeno[4,3-c]pyrazole The desired compound was prepared according to the procedure described for Example 1 using 2-(2-bromoethyl)-7-methoxy-4,4-dimethyl-1,4-dihydrochromeno[4,3-c]pyrazole (28 mg, 0.08 mmol) and benzoylpiperazine (16 mg, 0.08 mmol). Yellow oil (30 mg, 81%); $^1$H-NMR (400 MHz, $CDCl_3$) δ: 7.62 (d, J=8.4 Hz, 1H), 7.46-7.32 (m, 5H), 7.17 (s, 1H), 6.55 (dd, J=8.4, 2.5 Hz, J=6.6 Hz, 2H), 3.79 (s, 3H), 3.41-3.20 (m, 4H), 2.87 (t, J=6.6 Hz, 1H), 6.50 (d, Hz, 2H), 2.73-2.60 (m, 4H), 1.58 ppm (s, 6H, OC($CH_3$) 2); ($CDCl_3$) δ: 170.4 (CO), 160.8, 154.5, 142.9, 135.8, 129.9, 128.6, 127.1, 124.1, 123.0, 120.9, 111.1, 107.9, 103.1, 76.6, 57.9, 55.4, 53.7, 50.2, 47.9, 29.4 ppm; MS (ES$^+$, m/z) 447 [M+H]$^+$; HRMS $C_{26}H_{30}N_4O_3$: content. 446.2317, exp. 446.2311.

Example 5—Preparation of 1-(2-(4-(2-thienoyl)piperazinyl)ethyl)-1,4-dihydro-7-methoxy-4,4-dimethylchromeno[4,3-c]pyrazole The desired compound was prepared according to the procedure described for Example 1 using 1-(2-bromoethyl)-7-methoxy-4,4-dimethyl-1,4-dihydrochromeno[4,3-c]pyrazole (20 mg, 0.06 mmol) and 1-(2-thienoyl)piperazine trifluoroacetate (18 mg, 0.06 mmol). Yellow amorphous solid (6 mg, 23%); $^1$H-NMR (400 MHz, $CDCl_3$) δ: 7.49 (d, J=8.8 Hz, 1H), 7.44 (dd, J=5.0, 1.2 Hz, 1H), 7.28 (s, 1H), 7.23-7.21 (m, 6.54 (d, J=2.6 Hz, 1H), 4.54 (t, J=7.1 Hz, 2H), 7.03 (dd, J=5.0, 3.6 Hz, 1H), 6.61-6.58 (m, 1H), 6.57-3.82 (s, 3H), 3.77-3.64 (m, 4H), 2.93-2.87 (m, 2H), 2.67-2.43 (m, 4H), 1.58 ppm (s, 6H); $^{13}$C-NMR (101 MHz, $CDCl_3$) δ: 163.7, 161.0, 154.6, 150.3, 137.1, 132.8, 129.1, 128.9, 126.9, 122.7, 121.4, 109.1, 107.9, 104.1, 764, 57.4, 55.6, 53.6, 51.3, 49.5, 28.6 ppm; MS (ES$^+$, m/z) 453 [M+H]$^+$; HRMS C$_{24}$H$_{28}$N$_4$O$_3$S: content. 452.1882, exp. 452.1891.

Example 6—Preparation of 2-(2-(4-(2-thienoyl)piperazinyl)ethyl)-2,4-dihydro-7-methoxy-4,4-dimethylchromeno[4,3-c]pyrazole The desired compound was prepared according to the procedure described for Example 1 using 2-(2-bromoethyl)-7-methoxy-4,4-dimethyl-1,4-dihydrochromeno[4,3-c]pyrazole (30 mg, 0.09 mmol) and 1-(2-thienoyl)piperazine trifluoroacetate (28 mg, 0.09 mmol). Yellow solid (22 mg, 55%); mp: 163-165° C.; $^1$H-NMR (400 MHz, CDCl$_3$) δ: 7.62 (d, J=8.4 Hz, 1H), 7.44 (dd, J=5.0, 1.2 Hz, 1H), 7.25-7.23 (m, 1H), 7.20 (s, 6.55 (dd, J=8.4, 2.5 Hz, 1H), 6.51 (d, J=2.5 Hz, 1H), 4.27 (t, J=6.5), 7.03 (dd, 2H), 3.79 (s, 3H), 3.78-3.72 (m, 4H), 3.01-2.91 (m, 2H), 2.63-2.43 (m, 4H), 1.59 ppm (s, 6H); $^{13}$C-NMR (101 MHz, CDCl$_3$) δ: 163.8, 161.0, 154.6, 143.1, 137.0, 129.1, 128.9, 126.9, 124.3, 123.1, 121.0, 111.1, 108.0, 103.2, 76.7, 57.9, 55.5, 53.5, 50.2, 46.1, 29.5 ppm; MS (ES$^+$, m/z) 453 [M+H]$^+$; HRMS C$_{24}$H$_{28}$N$_4$O$_3$S: content. 452.1882, exp. 452, 1889.

Example 7: Preparation of 2-(2-(4-phenoxyacetylpiperazinyl) ethyl)-2,4-dihydro-7-methoxy-4,4-dimethylchromeno[4,3-c]pyrazole The desired compound was prepared according to the procedure described for Example 1 using 2-(2-bromoethyl)-7-methoxy-4,4-dimethyl-1,4-dihydrochromeno[4,3-c]pyrazole (30 mg, 0.09 mmol) and phenoxyacetylpiperazine (20 mg, 0.09 mmol). Orange solid (16 mg, 38%); mp: 177-179° C.; $^1$H-NMR (500 MHz, CD$_3$OD) δ: 7.56 (d, J=8.5 Hz, 1H), 7.52 (s, 1H), 7.31-7.21 (m, 2H), 7.00-6.90 (m, 3H), 6.56 (dd, J=8.5, 2.5 Hz, 1H), 6.48 (d, J=2.5 Hz, 1H), 4.76 (s, 2H), 4.26 (t, J=6.4 Hz, 2H), 3.77 (s, 3H), 3.63-3.50 (m, 4H), 2.84 (t, J=6.4 Hz, 2H), 2.56-2.46 (m, 4H), 1.56 ppm (s, 6H); $^{13}$C-NMR (126 MHz, CD$_3$OD) δ: 167.4, 161.1, 158.0, 154.5, 142.5, 129.1, 125.4, 122.3, 121.1, 120.5, 114.3, 110.4, 107.2, 102.8, 76.2, 66.1, 57.2, 54.3, 52.8, 52.3, 49.1, 44.7, 43.7, 28.0 ppm; MS (ES$^+$, m/z) 477 [M+H]$^+$; HRMS C$_{27}$H$_{32}$N$_4$O$_4$: content. 476.2423, exp. 476.2427.

Example 8: Preparation of 2-(2-(4-(2-tetrahydrofuroyl)piperazinyl)ethyl)-2,4-dihydro-7-methoxy-4,4-dimethylchromeno[4,3-c]pyrazole The desired compound was prepared according to the procedure described for Example 1 using 2-(2-bromoethyl)-7-methoxy-4,4-dimethyl-1,4-dihydrochromeno[4,3-c]pyrazole (30 mg, 0.09 mmol) and tetrahydrofuroylpiperazine (16 mg, 0.09 mmol). Yellow solid (14 mg, 36%); mp: 158-160° C.; $^1$H-NMR (500 MHz, CD$_3$OD) δ: 7.46 (d, J=8.5 Hz, 1H), 7.43 (s, 1H), 6.46 (dd, 2.5 Hz, 1H), 4.67-4.54 (m, 1H), 4.17 (t, J=6.5 Hz, 2H), 3.83-3.81 (m, 1H), 3.76-3.70 (m, 1H), 3.68 (s, 3H) 2H), 2.46-2.33 (m, 4H), 2.12-1.99 (m, 1H), 1.95-1.86 (m, 1H), 2.95 (m, 1H). 1.85-1.75 (m, 2H), 1.47 ppm (s, 6H); $^{13}$C-NMR (126 MHz, CD$_3$OD) δ: 171.3, 161.1, 154.5, 142.5, 125.4, 122.3, 120.5, 110.4, 107.2, 102.8, 76.2, 75.2, 68.7, 57.2, 54.3, 52.9, 52.3, 47.5, 44.9, 43.7, 28.8, 28.0, 25.1 ppm; MS (ES$^+$, m/z) 441 [M+H]$^+$; HRMS C$_{24}$H$_{32}$N$_4$O$_4$: content. 440.2423, exp. 440.2436.

Example 9: Preparation of 2-(2-(4-cyclohexylcarbonyl-piperazinyl)ethyl)-2,4-dihydro-7-methoxy-4,4-dimethylchromeno[4,3-c]pyrazole The desired compound was prepared according to the procedure described for Example 1 using 2-(2-bromoethyl)-7-methoxy-4,4-dimethyl-1,4-dihydrochromeno[4,3-c]pyrazole (30 mg, 0.09 mmol) and tetrahydrofuroylpiperazine (17 mg, 0.09 mmol). Yellow solid (25 mg, 62%); mp: 151-152° C.; $^1$H-NMR (400 MHz, CDCl$_3$) δ: 7.63 (d, J=8.5 Hz, 1H), 7.18 (s, 1H), 6.56 (dd, J=8.5, 2.5 Hz, 1H), 6.51 (d, J=2.4 Hz, 1H), 4.23 (t, J=6.6 Hz, 2H), 3.79 (s, 3H), 3.66-3.39 (m, 4H), 2.85 (t, J=6.6 Hz, 2H), 2.54-2.35 m, 4H), 1.82-1.75 (m, 1H), 1.73-1.61 (m, 4H), 1.59 (s, 6H), 1.57-1.42 ppm (m, 6H); $^{13}$C-NMR (101 MHz, CDCl$_3$) δ: 174.8, 160.9, 154.6, 143.0, 124.2, 123.1, 121.0, 111.2, 108.0, 103.2, 76.7, 58.0, 55.5, 53.2, 50.3, 45.6, 41.7, 30.6, 29.6, 26.1 ppm; MS (ES$^+$, m/z) 441 [M+H]$^+$; HRMS C$_{26}$H$_{36}$N$_4$O$_3$: content. 452.2787, exp. 452.2773.

Example 10—Preparation of 2-(2-(4-pivaloyl-piperazinyl)ethyl)-2,4-dihydro-7-methoxy-4,4-dimethylchromeno[4,3-c]pyrazole

The desired compound was prepared according to the procedure described for Example 1 using 2-(2-bromoethyl)-7-methoxy-4,4-dimethyl-1,4-dihydrochromeno[4,3-c]pyrazole (20 mg, 0.06 mmol) and pivaloyl piperazine (10 mg, 0.09 mmol). Yellow amorphous solid (8 mg, 32%); $^1$H-NMR (400 MHz, CDCl$_3$) δ: 7.62 (d, J=8.4 Hz, 1H), 7.18 (s, 1H), 6.55 (dd, J=8.4, 2.5 Hz, 1H), 6.51 (d, J=J=6.6 Hz, 2H), 3.79 (s, 3H), 3.63 (t, J=5.0 Hz, 4H), 2.84 (t, J=(t, J=5.0 Hz, 4H), 1.59 (s, 6H), 1.26 (s, 9H) ppm; $^{13}$C-NMR (101 MHz, CDCl$_3$) δ: 176.5, 160.9, 154.6, 142.9, 124.2, 123.1, 121.0, 111.2, 108.0, 103.2, 76.7, 58.0, 55.5, 53.6, 50.2, 45.3, 38.8, 29.5, 28.6 ppm. MS (ES$^+$, m/z) 427 [M+H]$^+$; HRMS C$_{24}$H$_{34}$N$_4$O$_3$: content. 426.2630, exp. 426.2618.

B. Preparation of 1-(2-(4-arylpiperazinyl)acetamidomethyl)-1,4-dihydro-7-methoxy-4,4-dimethylchromene[4,3-c]pyrazoles of Formula (V) and the 2-(2-(4-arylpiperazinyl) acetamidomethyl)-2,4-dihydro-7-methoxy-4,4-dimethylchromeno[4,3-c]pyrazoles of Formula (I) wherein R$^1$ is an Aryl

For the synthesis of 1-(2-(4-arylpiperazinyl)acetamidomethyl)-1,4-dihydro-7-methoxy-4,4-dimethylchromene[4,3-c]pyrazoles and 2-(2-4-arylpiperazinyl)acetamidomethyl)-2,4-dihydro-7-methoxy-4,4-dimethylchromeno[4,3-c]pyrazoles of formula (I) in which R$^1$ is an aryl, 7-methoxy-4,4-dimethyl-1,4-dihydrochromeno[4,3-c]pyrazole was alkylated with the corresponding N-hydroxymethyl-2-(4-phenylpiperazinyl)acetamide.

This procedure is summarized in the following scheme (III):

Scheme (III)

-continued

The N-hydroxymethyl-2-(4-phenylpiperazinyl)acetamides were prepared by N-alkylation of the phenylpiperazine with the corresponding 2-chloro-N-hydroxymethylacetamide.

This procedure is summarized in the following scheme (IV):

Scheme (IV)

Preparation of N-hydroxymethyl-2-(4-phenylpiperazinyl)acetamides

A solution of 2-chloro-N-hydroxymethylacetamide (2 eq) in acetonitrile is added to a mixture of the corresponding phenylpiperazine (1 eq) with $K_2CO_3$ (1.5 eq) in acetonitrile. The mixture was heated at reflux for 2-5 h. The solvent was evaporated in vacuum. The crude oil dissolved in AcOEt was washed with water, dried with $MgSO_4$ and the solvent was evaporated under vacuum. Flash chromatography on silica gel (EtOAc) afforded the corresponding N-hydroxymethyl-2-(4-phenylpiperazinyl)acetamide.

N-Hydroxymethyl-2-(4-phenylpiperazinyl)acetamide (41%). mp: 112-114° C.; $^1$H-NMR (400 MHz, $CDCl_3$) δ: 8.10-8.02 (brs, 1H), 7.39-7.22 (m, 2H), 7.06-6.85 (m, 3H), 4.82 (s, 2H), 3.28-3.19 (m, 4H), 3.13 (s, 2H), 2.90-2.57 ppm (m, 4H); $^{13}$C-NMR (101 MHz, $CDCl_3$) δ: 173.6, 151.5, 129.8, 129.7, 120.5, 119.3, 116.7, 73.1, 62.0, 54.1, 53.7, 50.9, 49.8 ppm; MS ($ES^+$, m/z) 250 $[M+H]^+$; Anal. $C_{13}H_{19}N_3O_2$: content. C, 62.63%, H, 7.68%, exp. C, 62.41%, H, 7.83%.

N-Hydroxymethyl-2-(4-(2-methoxyphenyl)piperazinyl)acetamide (63%). mp: 134-136° C.; $^1$H-NMR (400 MHz, $CDCl_3$) δ: 8.14-8.11 (br s, 1H), 7.03-6.96 (m, 2H), 6.89-6.78 (m, 2H), 4.79 (s, 2H), 3.94-3.64 (m, 5H), 3.17-2.89 (m, 4H), 2.84-2.66 ppm (m, 4H); $^{13}$C-NMR (101 MHz, $CDCl_3$) δ: 171.4, 151.7, 140.4, 122.6, 120.5, 117.6 and 110.8, 63.0, 61.0, 54.8, 53.6, 53.2, 51.0, 50.1 ppm; MS ($ES^+$, m/z) 280 $[M+H]^+$; Anal. $C_{14}H_{21}N_3O_3$: content. C, 60.20%, H, 7.58%, Found: C, 60.31%, H, 7.72%.

N-Hydroxymethyl-2-(4-(2,3-dimethylphenyl)piperazinyl)acetamide (25%). mp: 126-127° C.; $^1$H NMR (400 MHz, $CDCl_3$) δ: 8.19-8.14 (brs, 1H), 7.07 (t, J=7.6 Hz, 1H), 6.98-6.90 (m, 2H), 5.59-5.57 (br s, 1H, 2H), 2.94-2.92 (m, 4H), 2.77-2.73 (m, 4H), 2.27 (s, 3H), 2.21 (s, 3H), 2.21 (s, 2H) ppm; $^{13}$C-NMR (101 MHz, $CDCl_3$) δ: 173.8, 172.0, 151.2, 138.0, 131.3, 125.8, 125.1, 74.6, 67.3, 63.7, 61.5, 54.1, 52.2, 20.6, 13.9 ppm; MS ($ES^+$, m/z) 278 $[M+H]^+$; Anal. $C_{15}H_{23}N_3O_2$: content. C, 64.96%, H, 8.36%, Found: C, 65.09%, H, 8.03%.

N-Hydroxymethyl-2-(4-(4-methoxyphenyl)piper azinyl)acetamide (24%). mp: 140-143° C.; $^1$H-NMR (400 MHz, $CDCl_3$) δ: 7.09-6.95 (m, 2H), 6.71-6.54 (m, 2H), 4.83 (s, 2H), 3.78-3.60 (m, 5H), 3.14-3.05 (m, 4H), 2.77-2.71 ppm (m, 4H); $^{13}$C-NMR (101 MHz, $CDCl_3$) δ: 173.0, 152.4, 143.6, 123.4, 122.1, 118.6, 112.3, 65.7, 63.2, 55.1, 54.3, 53.8, 51.8, 51.2 ppm; MS ($ES^+$, m/z) 280 $[M+H]^+$; Anal. $C_{14}H_{21}N_3O_3$: content. C, 60.20%, H, 7.58%, exp. C, 60.56%, H, 7.25%.

General Procedure to Prepare 1-(2-(4-arylpiperazinyl)acetamidomethyl)-1,4-dihydro-7-methoxy-4,4-dimethylchromeno[4,3-c]pyrazoles of Formula (V) and 2-(2-(4-arylpiperazinyl) acetamidomethyl)-2,4-dihydro-7-methoxy-4,4-dimethylchromeno[4,3-c]pyrazoles of formula (IV)

A solution of 7-methoxy-4,4-dimethyl-1,4-dihydrochromeno[4,3-c]pyrazole (1 eq) in anhydrous THF was added slowly to a suspension of NaH (3 eq) in anhydrous THF at 0° C. under nitrogen atmosphere. After 10 min. of stirring at room temperature was added the corresponding N-hydroxymethyl-2-(4-phenylpiperazinyl)acetamide (2 eq). The reaction mixture was heated at reflux for 12-72 h. The solvent was evaporated in vacuum. The crude oil dissolved in AcOEt was washed with water, dried with $MgSO_4$ and the solvent was evaporated under vacuum. Semipreparative chromatography on $C_{18}$-silica ($CH_3CN/H_2O$) led to the separation of 1-(2-(4-arylpiperazinyl)acetamidomethyl)-1,4-dihydro-7-methoxy-4,4-dimethylchromene[4,3-c]pyrazole and the corresponding 2-(2-(4-arylpiperazinyl)acetamidomethyl)-2,4-dihydro-7-methoxy-4,4-dimethylchromeno[4,3-c]pyrazole.

Example 11. Preparation of 1-(2-(4-phenylpiperazinyl)acetamidomethyl)-1,4-dihydro-7-methoxy-4,4-dimethylchromeno[4,3-c]pyrazole The desired compound was prepared according to the general mode of preparation described above.

White solid (13%). mp: 196-198° C.; $^1$H-NMR (500 MHz, CDCl$_3$) δ: 8.02-7.97 (brt, J=6.3 Hz, 1H), 7.76 (d, J=8.7 Hz, 1H), 7.26 (s, 1H), 6.85-6.74, 6.55 (dd, J=8.6, 2.6 Hz, 2H), 6.53-6.46 (m, 2H), 6.45 (d, J=2.5 Hz, 1H), 5.73 (d, J=6.3 Hz, 2H), 3.71 (s, 3H), 3.13-3.07 (m, 4H), 3.03 (s, 2H), 2.57-2.48 (m, 4H), 1.52 (s, 6H) ppm; $^{13}$C-NMR (126 MHz, CDCl$_3$) δ: 170.2, 165.1, 161.0, 154.3, 149.2, 133.8, 132.5, 129.1, 123.3, 121.4, 120.0, 116.2, 107.8, 103.85, 76.73, 61.3, 55.3, 54.32, 53.4, 49.1, 28.24 ppm; MS (ES$^+$, m/z) 462 [M+H]$^+$; HRMS C$_{26}$H$_{31}$N$_5$O$_3$: content. 461.2426, exp. 461.2433.

Example 12. Preparation of 2-(2-(4-phenylpiperazinyl)acetamidomethyl)-2,4-dihydro-7-methoxy-4,4-dimethylchromeno[4,3-c]pyrazole The desired compound was prepared according to the general mode of preparation described above.

Amorphous solid (5%); $^1$H-NMR (500 MHz, CD$_3$OD) δ: 8.44-8.40 (br s, 1H), 7.51 (d, J=8.5, 1H), 7.44 (s, 1H), 7.15-7.04 (m, 2H), 6.82 ((d, J=7.4, 1.0 Hz, 1H), 6.47 (dd, J=8.5, 2.4 Hz, 1H), 6.39 (d, J=2.4 Hz, 1H) (M, 4H), 3.02 (s, 2H), 2.55-2.49 (m, 4H), 1.46 (s, 6H) ppm; $^{13}$C-NMR (126 MHz, CD$_3$OD) δ: 173.7, 162.7, 156.1, 152.7, 144.6, 130.0, 126.6, 123.9, 122.4, 121.1, 117.5, 111.5, 108.8, 104.2, 77.6, 62.1, 55.8, 55.4, 54.3, 54.2, 50.5, 50.4, 29.3 ppm; MS (ES$^+$, m/z) 462 [M+H]$^+$; HRMS C$_{26}$H$_{31}$N$_5$O$_3$: content. 461.2426, exp. 461.2421.

Example 13. Preparation of 1-(2-(4-(2-methoxyphenyl)piperazinyl)acetamidomethyl)-1,4-dihydro-7-methoxy-4,4-dimethylchromeno[4,3-c]pyrazole The desired compound was prepared according to the general mode of preparation described above.

White amorphous solid (3%); $^1$H-NMR (500 MHz, CDCl$_3$) δ: 7.35 (d, J=8.1 Hz, 1H), 7.16 (s, 1H), 6.71-6.59 (m, 4H), 6.42 (dd, J=8.1, 2.4 Hz, 2H), 3.59 (s, 3H), 3.54 (s, 3H), 3.29 (s, 2H), 3.10-3.03 (m, 4H)), 2.98-2.86 (m, 4H), 1.69 (s, 6H) ppm; $^{13}$C-NMR (126 MHz, CDCl$_3$) δ: 175.0, 160.4, 155.6, 155.1, 149.5, 147.1, 130.2, 127.5, 124.9, 118.7, 116.9, 116.3, 113.3, 111.4, 106.8, 104.2, 75.8, 61.4, 55.9, 55.1, 54.0, 53.7, 51.3, 25.9 ppm; MS (ES$^+$, m/z) 492 [M+H]$^+$; HRMS C$_{27}$H$_{33}$N$_5$O$_4$: content. 491.2532, exp. 491, 2528.

Example 14. Preparation of 2-(2-(4-(2-methoxyphenyl)piperazinyl)acetamidomethyl)-2,4-dihydro-7-methoxy-4,4-dimethylchromeno[4,3-c]pyrazole The desired compound was prepared according to the general mode of preparation described above.

Yellow oil (8%); $^1$H-NMR (500 MHz, CDCl$_3$) δ: 7.04 (d, J=7.5 Hz, 1H), 6.91 (s, 1H), 6.69-6.51 (m, 5H), 6.42 (d, J=2.6 Hz, 1H), 3.64 (s, 3H), 3.59 (s, 3H), 3.16 (s, 2H), 2.92-2.89 (m, 4H), 2.76-2.70 (m, 4H), 1.54 (s, 6H) ppm; $^{13}$C-NMR (126 MHz, CDCl$_3$) δ: 173.2, 163.1, 156.7, 153.1, 148.1, 144.9, 132.6, 126.1, 125.6, 120.9, 118.2, 117.5, 114.0, 110.6, 109.4, 106.0, 75.3, 60.2, 56.8, 56.1, 54.6, 52.5, 50.7, 26.4 ppm; MS (ES$^+$, m/z) 492 [M+H]$^+$; HRMS C$_{27}$H$_{33}$N$_5$O$_4$: content. 491.2532, exp. 491.2540.

Example 15: Preparation of 1-(2-(4-(2,3-dimethylphenyl)piperazinyl)acetamidomethyl)-1,4-dihydro-7-methoxy-4,4-dimethylchromeno[4,3-c]pyrazole The desired compound was prepared according to the general mode of preparation described above.

Yellow oil (2%); $^1$H-NMR (500 MHz, CDCl$_3$) δ: 8.08-8.02 (brt, J=6.4 Hz, 1H), 7.76 (d, J=8.1 Hz, 1H), 7.50 (s, 1H), 6.94 (t, J=(D, J=7.7 Hz, 1H), 6.61 (dd, J=8.1, 2.6 Hz, 1H), 6.48 (d, J=7.5 Hz, 2.6 Hz, 1H), 5.61 (d, J=6.4 Hz, 2H), 3.84 (s, 3H), 3.08 (s, 2H), 2.77-2.69 (m, 4H), 2.64-2.59 (m, 4H), 2.31 (s, 3H), 2.27 (s, 3H), 1.48 (s, 6H) ppm; $^{13}$C-NMR (126 MHz, CDCl$_3$) δ: 169.8, 162.4, 156.0, 151.3, 144.2, 140.3, 132.5, 126.1, 125.0, 123.9, 123.1, 121.8, 117.2, 109.8, 108.4, 104.9, 75.7, 61.3, 56.0, 54.7, 53.3, 51.9, 28.8, 19.7, 14.1 ppm MS (ES$^+$, m/z) 490 [M+H]$^+$; HRMS C$_{28}$H$_{35}$N$_5$O$_3$: content. 489.2739, exp. 489.2746.

Example 16. Preparation of 2-(2-(4-(2,3-dimethylphenyl)piperazinyl)acetamidomethyl)-2,4-dihydro-7-methoxy-4,4-dimethylchromeno[4,3-c]pyrazole The desired compound was prepared according to the general mode of preparation described above.

White solid (4%); mp: 199-201° C.; $^1$H-NMR (500 MHz, CDCl$_3$) δ: 8.22-8.17 (brt, J=6.9 Hz, 1H), 7.62 (d, J=8.5 Hz, 1H), 7.42 (s, 1H), 7.08 (t, J=1H), 6.87 (d, J=7.7 Hz, 1H), 6.57 (dd, J=8.5, 2.5 Hz, 1H), 6.51 (d, J=2.5 Hz, 1H), 5.54 (d, J=6.9 Hz, 2H), 3.79 (s, 3H), 3.11 (s, 2H), 2.87 (t, J=4.8 Hz, 4H), 2.63 (t, J=4.8 Hz, 4H), 2.25 (s, 3H), 2.18 (s, 3H), 1.58 (s, 6H) ppm; $^{13}$C-NMR (126 MHz, CDCl$_3$) δ: 171.5, 161.0, 154.6, 151.1, 143.5, 138.0, 131.2, 125.8, 125.2, 124.7, 122.8, 121.5, 116.6, 110.4, 108.0, 103.0, 76.5, 61.4, 55.3, 54.2, 53.9, 52.0, 29.1, 20.6, 13.8 ppm; MS (ES$^+$, m/z) 490 [M+H]$^+$; HRMS C$_{28}$H$_{35}$N$_5$O$_3$: content. 489.2739, exp. 489.2750.

Example 17. Preparation of 1-(2-(4-(4-methoxyphenyl)piperazinyl)acetamidomethyl)-1,4-dihydro-7-methoxy-4,4-dimethylchromene[4,3-c]pyrazole The desired compound was prepared according to the general mode of preparation described above.

Yellow oil (14%); $^1$H-NMR (500 MHz, CDCl$_3$) δ: 7.50-7.48 (brt, J=5.1 Hz, 1H), 6.81-6.76 (m, 4H), 6.76-6.68 (m, 2H), 6.47 (dd, J=5.1 Hz, 2H), 3.68 (s, 3H), 3.63 (s, 3H), 3.01 (s, 2H), 2.97-2.94 (m, 4H), 2.55-2.47 (m, 4H), 1.46 (s, 6H) ppm; $^{13}$C-NMR (126 MHz, CDCl$^3$) δ: 172.2, 161.2, 154.6, 154.2, 145.2, 143.2, 125.1, 122.4, 120.9, 118.7, 113.8, 110.0, 107.3, 102.7, 76.1, 60.6, 54.4, 54.3, 53.9, 52.9 50.4, 27.8 ppm; MS (ES$^+$, m/z) 492 [M+H]$^+$; HRMS C$_{27}$H$_{33}$N$_5$O$_4$: content. 491.2532, exp. 491.2524.

C. Biological Assays

In the present invention, the activity of the compounds of the invention on the GPR55 receptor was assessed by performing in vitro assays with real-time cell impedance measurements (xCELLigence experiments). These assays were performed on a HEK293 human embryonic kidney cell line overexpressing the recombinant GPR55 receptor in stable form (hGPR55-HEK293). The cells were seeded one day prior to carrying out the stimulation with the exemplary compounds of the present invention.

GPR55 Agonist Activity.

Activation of the GPR55 receptor by an agonist compound causes a cellular impedance detected by the system and compared to lysophosphatidylinositol (LPI), a reference GPR55 ligand. The effect of LPI measured at a concentration of 1 μM was set at 100%. The maximum response was observed at 5 minutes after the addition of the example compound of the invention. Therefore, dose-response curves were determined at this time. Cell impedance values were normalized for each well, just prior to addition of the inventive compound of the invention to be evaluated. The EC50 (nM) effective concentration values of some exemplary compounds of the present invention and the percentage of the maximum effect Emax (%) relative to the LPI activity are given below (Table 1) by way of illustration:

TABLE 1

Agonist action of compound examples of the patent on GPR55 as measured by the xCELLigence system.

| Examples | GPR55 | |
|---|---|---|
| | $EC_{50}$ (nM) | $E_{max}$ (%) |
| 2 | 0.88 (0.05-14.56) | 43 (31-54) |
| 4 | 0.60 (0.12-3.03) | 51 (42-60) |
| 6 | 0.51 (0.06-4.22) | 45 (36-54) |
| 7 | 1.28 (0.20-9.46) | 52 (41-63) |
| 8 | 0.40 (0.03-4.61) | 51 (40-62) |
| 9 | 8.67 (1.18-63.45) | 47 (36-58) |
| 10 | 0.69 (0.06-7.63) | 49 (37-62) |
| 14 | 6.36 (0.98-41.52) | 51 (36-67) |
| LPI | 2.82 (0.64-12.30) | 100 (81-118) |

These values represent the mean with a 95% confidence interval calculated with 4 independent experiments performed in duplicate.

The compounds of examples 2, 4, 6-10, and 14 are partial agonists of the GPR55 receptor.

GPR55 Antagonist Activity.

The ability of the exemplary compounds of the patent to inhibit LPI-mediated GPR55 receptor stimulation has been evaluated. The EC50 (nM) effective concentration values of LPI are given (Table 2) by way of illustration in the presence of certain exemplary compounds of the present invention at a concentration of 1 μM and the percentage of the maximum effect Emax (%) relative to LPI activity:

TABLE 2

Antagonist action of compound examples of the patent on the effect produced by LPI through GPR55 and measured by the xCELLigence system.

| Examples | GPR55 | |
|---|---|---|
| | $EC_{50}$ (nM) | $E_{max}$ (%) |
| LPI + 7 | 18.2 (4.6-71.1) | 100 (91-115) |
| LPI + 8 | 24.6 (7.9-66.8) | 102 (91-106) |
| LPI + 9 | 25.4 (6.6-96.7) | 99 (90-113) |
| LPI + 10 | 21.9 (5.5-87.6) | 100 (86-114) |
| LPI | 1.6 (0.6-4.2) | 99 (90-108) |

Values represent the mean with a 95% confidence interval calculated with 4 independent experiments performed in duplicate. Significant differences with respect to LPI values are considered due to lack of overlap of confidence intervals.

The compounds of Examples 7-10 are antagonists of the GPR55 agonist effect produced by LPI.

As a control experiment, it was found that the exemplary compounds of the present invention have no action on HEK293 cells that do not overexpress the GPR55 receptor. None of the compounds showed cell impedance.

With respect to cannabinoid activity, no exemplary compound of the present invention binds the cannabinoid receptor CB1. In what refers to the CB2 receptor binding, from all of the exemplary compounds, only 3 examples have affinity constant with a value of less than micromolar: example 2 (698±107 nM), example 6 (15.4±7.8 nM), example 9 (523±144 nM).

D. Pharmacokinetic Properties: In Silico Predictions

The pharmacokinetic profile of the exemplary compounds of the invention was determined by in silico prediction of physicochemical parameters using the QikProp program implemented in Maestro (Schrödinger, LLC, New York, USA). The values shown in Table 3 by the exemplary compounds of the patent follow Lipinski rules. Therefore, they are believed to be acceptable candidates for being part of a pharmaceutical composition.

TABLE 3

Physicochemical descriptors calculated by QikProp 3.5 integrated in Master (Schrödinger, LLC, New York, USA) [95% drug range].

| Comp. | QPlogS[a] | QlogBB[b] | QPlogHERG[c] | QPPCaco[d] | % Human Oral Absorbtion in GI[e] |
|---|---|---|---|---|---|
| 1 | −4.1 | −0.05 | −6.779 | 559 | 100 |
| 2 | −4.1 | 0.08 | −7.051 | 774 | 100 |
| 3 | −4.7 | 0.01 | −7.076 | 641 | 100 |
| 4 | −5.2 | 0.08 | −7.524 | 796 | 100 |
| 5 | −4.8 | 0.12 | −6.755 | 642 | 100 |
| 6 | −4.9 | 0.25 | −7.085 | 880 | 100 |
| 7 | −4.4 | 0.03 | −6.334 | 589 | 100 |
| 8 | −2.9 | 0.13 | −5.028 | 512 | 89 |
| 9 | −4.6 | 0.30 | −5.133 | 832 | 100 |
| 10 | −3.9 | 0.27 | −5.041 | 750 | 100 |
| 11 | −4.8 | 0.11 | −5.803 | 529 | 100 |
| 12 | −4.7 | 0.10 | −6.064 | 504 | 100 |
| 13 | −4.8 | 0.05 | −5.588 | 529 | 100 |
| 14 | −4.7 | 0.04 | −5.842 | 504 | 100 |

TABLE 3-continued

Physicochemical descriptors calculated by QikProp 3.5 integrated in Master (Schrödinger, LLC, New York, USA) [95% drug range].

| Comp. | QPlogS[a] | QlogBB[b] | QPlogHERG[c] | QPPCaco[d] | % Human Oral Absorbtion in GI[e] |
|---|---|---|---|---|---|
| 15 | −5.5 | 0.10 | −5.543 | 529 | 100 |
| 16 | −5.5 | 0.09 | −5.789 | 504 | 100 |
| 17 | −4.5 | 0.06 | −5.395 | 529 | 100 |
| LPI | −3.4 | −4.84 | −4.139 | 5 | 11 |

[a]Prediction of solubility in water [−6.5/0.5];
[b]Prediction of blood-brain barrier passage [−3.0/1.2];
[c]HERG K+ channel (log IC$_{50}$) [>−5];
[d]Apparent permeability in nm/s in Caco-2 cells [<25 low, >500 excellent];
[e]Human oral absorption in the gastrointestinal tract (GI) [<25% low].

The invention claimed is:

1. A compound of formula (II) or formula (III):

Formula (II)

Formula (III)

or a tautomer, a pharmaceutically acceptable salt or solvate thereof;

wherein:

$R^1$ is selected from the group consisting of a phenyl group, a phenyl group substituted by a $C_1$-$C_4$ alkyl, a phenyl group substituted by a $C_1$-$C_4$ alkyloxy, and a —C(O)$R^3$ group; wherein $R^3$ is selected from the group consisting of phenyl, furan, thiophene, tetrahydrofuran, cyclohexyl, $C_1$-$C_4$ alkyl, and a —(CH$_2$)$_n$—O-phenyl wherein n is a value selected from 1,2, 3 or 4, and $R^2$ is a $C_1$-$C_4$ alkylene or a —$R^4$—C(O)—NH—$R^5$— group, wherein $R^4$ and $R^5$ are the same or different- $C_1$-$C_6$ alkylene.

2. The compound according to claim 1, wherein $R^1$ is a —C(O)$R^3$ group.

3. The compound according to claim 2, wherein $R^3$ is phenyl.

4. The compound according to claim 2, wherein $R^3$ is selected from furan, thiophene or tetrahydrofuran.

5. The compound according to claim 2, wherein $R^3$ is cyclohexyl.

6. The compound according to claim 2, wherein $R^3$ is $C_1$-$C_4$ alkyl.

7. The compound according to claim 1, wherein $R^2$ is $C_1$-$C_4$ alkylene.

8. The compound according to claim 7, wherein $R^2$ is ethylene.

9. The compound according to claim 1, selected from the group consisting of:

1-(2-(4-(2-furoyl)piperazinyl)ethyl)-1,4-dihydro-7-methoxy-4,4-dimethylchromeno[4,3-c]pyrazole;

2-(2-(4-(2-furoyl)piperazinyl)ethyl)-2,4-dihydro-7-methoxy-4,4-dimethylchromeno [4,3-c]pyrazole;

1-(2-(4-benzoyl-piperazinyl)ethyl)-1,4-dihydro-7-methoxy-4,4-dimethylchromeno[4,3-c]pyrazole;

2-(2-(4-benzoyl-piperazinyl)ethyl)-2,4-dihydro-7-methoxy-4,4-dimethylchromeno [4,3-c]pyrazole;

1-(2-(4-(2-thienoyl)piperazinyl)ethyl)-1,4-dihydro-7-methoxy-4,4-dimethylchromeno[4,3-c]pyrazole;

2-(2-(4-(2-thienoyl)piperazinyl)ethyl)-2,4-dihydro-7-methoxy-4,4-dimethylchromeno [4,3-c]pyrazole;

2-(2-(4-phenoxyacetylpiperazinyl)ethyl)-2,4-dihydro-7-methoxy-4,4-dimethylchromeno[4,3-c]pyrazole;

2-(2-(4-(2-tetrahydrofuroyl)piperazinyl)ethyl)-2,4-dihydro-7-methoxy-4,4-dimethylchromeno[4,3-c]pyrazole;

2-(2-(4-cyclohexylcarbonyl-piperazinyl)ethyl)-2,4-dihydro-7-methoxy-4,4-dimethylchromeno [4,3-c]pyrazole;

2-(2-(4-pivaloyl-piperazinyl)ethyl)-2,4-dihydro-7-methoxy-4,4-dimethylchromeno [4,3-c]pyrazole;

1-(2-(4-phenylpiperazinyl)acetamidomethyl)-1,4-dihydro-7-methoxy-4,4-dimethylchromeno [4,3-c]pyrazole;

1-(2-(4-(2-methoxyphenyl)piperazinyl)acetamidomethyl)-1,4-dihydro-7-methoxy-4,4-dimethylchromeno [4,3-c]pyrazole;

1-(2-(4-(2,3-dimethylphenyl)piperazinyl)acetamidomethyl)-1,4-dihydro-7-methoxy-4,4-dimethylchromeno [4,3-c]pyrazole;

1-(2-(4-(4-methoxyphenyl)piperazinyl)acetamidomethyl)-1,4-dihydro-7-methoxy-4,4-dimethylchromeno [4,3-c]pyrazole;

2-(2-(4-phenylpiperazinyl)acetamidomethyl)-2,4-dihydro-7-methoxy-4,4-dimethylchromeno [4,3-c]pyrazole;

2-(2-(4-(2-methoxyphenyl)piperazinyl)acetamidomethyl)-2,4-dihydro-7-methoxy-4,4-dimethylchromeno [4,3-c]pyrazole;

2-(2-(4-(2,3-dimethylphenyl)piperazinyl)acetamidomethyl)-2,4-dihydro-7-methoxy-4,4-dimethylchromeno [4,3-c]pyrazole.

10. The compound according to claim 1, wherein $R^1$ is a phenyl substituted by a $C_1$-$C_4$ alkyl or a $C_1$-$C_4$ alkyloxy.

11. The compound according to claim 10, wherein $R^1$ is a phenyl substituted by at least one methyl or a methoxy.

12. The compound according to claim 1, wherein $R^2$ is a —$R^4$—C(O)—NH—$R^5$— group, wherein $R^4$ and $R^5$ are the same or different $C_1$-$C_4$ alkylene.

13. The compound according to claim 12, wherein $R^4$ and $R^5$ are methylene.

14. A pharmaceutical composition comprising at least one compound according to claim 1.

15. The pharmaceutical composition according to claim 14, which further comprises a pharmaceutically acceptable carrier, excipient or vehicle.

16. A method for the treatment of a disorder associated with a GPR55 receptor, comprising administering to a subject in need thereof an effective amount of a compound according to claim 1 by modulating the GPR55 receptor, wherein the disorder is selected from diabetes, Parkinson's disease, multiple sclerosis, neuropathic pain, and osteoporosis.

17. A reagent in biological assays related to a GPR55 receptor which comprises a compound according to claim 1.

18. The compound of claim 1, wherein $R^1$ is a —C(O)$R^3$ group, wherein $R^3$ is selected from the group consisting of phenyl, furan, thiophene, tetrahydrofuran, cyclohexyl, and $C_1$-$C_4$ alkyl, and $R^2$ is a $C_1$-$C_4$ alkylene.

19. The compound of claim 1, wherein $R^1$ is selected from the group consisting of a phenyl group, a phenyl group substituted by a $C_1$-$C_4$ alkyl, a phenyl group substituted by a $C_1$-$C_4$ alkyloxy, and $R^2$ is a $C_1$-$C_4$ alkylene or $R^4$—C(O)—NH—$R^5$— group, wherein $R^4$ and $R^s$ are the same or different $C_1$-$C_4$ alkylene.

* * * * *